(12) United States Patent
Jablonski et al.

(10) Patent No.: US 8,394,834 B2
(45) Date of Patent: Mar. 12, 2013

(54) PYRROLIDINES AS NK3 RECEPTOR ANTAGONISTS

(75) Inventors: Philippe Jablonski, Steinbrunn-le-Haut (FR); Henner Knust, Rheinfelden (DE); Matthias Nettekoven, Grenzach-Wyhlen (DE); Angelique Patiny-Adam, Rosenau (FR); Hasane Ratni, Habsheim (FR); Claus Riemer, Freiburg (DE)

(73) Assignee: Hoffman-La Roche Inc., Nutley, NJ (US)

(*) Notice: Subject to any disclaimer, the term of this patent is extended or adjusted under 35 U.S.C. 154(b) by 82 days.

(21) Appl. No.: 12/856,691

(22) Filed: Aug. 16, 2010

(65) Prior Publication Data

US 2011/0053948 A1 Mar. 3, 2011

(30) Foreign Application Priority Data

Aug. 25, 2009 (EP) .................... 09168630

(51) Int. Cl.
*A61K 31/4439* (2006.01)
*C07D 401/14* (2006.01)
(52) U.S. Cl. .............. 514/333; 546/268.1; 546/276.4; 546/279.1; 544/224; 544/238; 514/318; 514/332
(58) Field of Classification Search ......... 546/184, 546/193, 268.1, 276.4, 279.1; 544/224, 238; 514/315, 318, 332, 333
See application file for complete search history.

(56) References Cited

U.S. PATENT DOCUMENTS 7,468,437 B2 * 12/2008 DeVita et al. .......... 544/358
7,812,021 B2 * 10/2010 Jablonski et al. ....... 514/235.5

FOREIGN PATENT DOCUMENTS

| WO | 2009/019163 | 2/2009 |
| WO | 2009/024502 | 2/2009 |
| WO | 2009/150110 | 12/2009 |

OTHER PUBLICATIONS

Tooney et al., Neurosci. Letters (2000) vol. 283 pp. 185-188.
Giardina et al., Exp. Opin. Ther. Patents (2000) vol. 10, pp. 939-960.
Jung et al., Neuroscience (1996) vol. 74 pp. 403-414.
Marco et al., Neuropeptides (1998) vol. 32 pp. 481-488.
Kamali, F., Current Opinion in Investigational Drugs (2001) vol. 2(7) pp. 950-956.
(Tranlsation of Israeli Off Action in Corres. Israeli Appl. 217759 Feb. 29, 2012).
Market Report from Decision Resources, Inc. (Psychiatric Disorders Study 4, Schizophrenia Jun. 2003).

* cited by examiner

*Primary Examiner* — Golam M M Shameem
(74) *Attorney, Agent, or Firm* — George W. Johnston; Patricia S. Rocha-Tramaloni; Kimberly J. Prior

(57) ABSTRACT

The present invention relates to a compounds of formula I

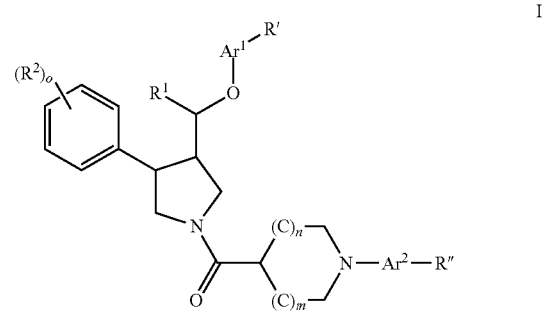

wherein $R^1$, $R^2$, $Ar^1$, $Ar^2$, $R'$, $R''$, m, n, and o are defined in the specification or to a pharmaceutically active salt, racemic mixture, enantiomer, optical isomer or to tautomeric form thereof. The present compounds are high potential NK-3 receptor antagonists for the treatment of depression, pain, psychosis, Parkinson's disease, schizophrenia, anxiety and attention deficit hyperactivity disorder (ADHD).

9 Claims, No Drawings

PYRROLIDINES AS NK3 RECEPTOR ANTAGONISTS

PRIORITY TO RELATED APPLICATION(S)

This application claims the benefit of European Patent Application No. 09168630.3, filed Aug. 25, 2009, which is hereby incorporated by reference in its entirety.

BACKGROUND OF THE INVENTION

The three main mammalian tachykinins, substance P (SP), neurokinin A (NKA) and neurokinin B (NKB) belong to the family of neuropeptides sharing the common COOH-terminal pentapeptide sequence of Phe-X-Gly-Leu-Met-$NH_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters,* 2000, 283, 185-188; *Exp. Opin. Ther. Patents* 2000, 10, 939-960; *Neuroscience,* 1996, 74, 403-414; *Neuropeptides,* 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs,* 2001, 2(7), 950-956 and *Psychiatric Disorders Study* 4, *Schizophrenia,* June 2003, Decision Recourses, Inc., Waltham, Mass.). The proposed drug SR 142,801 has been shown in a phase II trial as active on positive symptoms of schizophrenia, such as altered behaviour, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs,* 2001, 2(7), 950-956 956 and *Psychiatric Disorders Study* 4, *Schizophrenia,* June 2003, Decision Recourses, Inc., Waltham, Mass.).

SUMMARY OF THE INVENTION

The present invention provides compounds of formula I

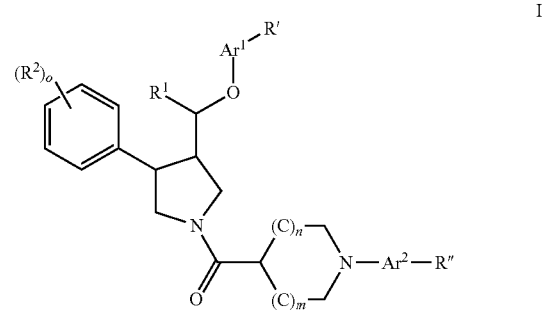

wherein
$R^1$ is hydrogen or lower alkyl;
$R^2$ is hydrogen, lower alkyl, lower alkyl substituted by halogen or is halogen or CN, and wherein o is 2 each $R^2$ is the same or different;
$Ar^1$ is aryl or heteroaryl;
$Ar^2$ is aryl or heteroaryl;
R' and R" are each independently hydrogen, lower alkyl, lower alkoxy, halogen, C(O)-lower alkyl, cyano or lower alkyl substituted by halogen;
m is 0, 1, or 2 when n is 0; or
m is 0 or 1 when n is 1;
n is 0 or 1; and
o is 1 or 2;
or pharmaceutically active salts, racemic mixtures, enantiomers, optical isomers or to tautomeric forms thereof.

The invention includes all stereoisomeric forms, including individual diastereoisomers and enantiomers of the compound of formula I as well as racemic and non-racemic mixtures thereof.

The present invention also provides pharmaceutical compositions containing compounds of formula I or their pharmaceutically acceptable salts, and a pharmaceutically acceptable carrier. The invention further comprises methods for the manufacture of the compounds and compositions of the invention. The invention comprises methods for the treatment of illnesses such as depression, pain, bipolar disorders, psychosis, Parkinson's disease, schizophrenia, anxiety and attention deficit hyperactivity disorder (ADHD).

The present compounds are high potential NK-3 receptor antagonists for the treatment of depression, pain, psychosis, Parkinson's disease, schizophrenia, anxiety and attention deficit hyperactivity disorder (ADHD).

The preferred indications using the compounds of the present invention are depression, psychosis, Parkinson's disease, schizophrenia, anxiety and attention deficit hyperactivity disorder (ADHD).

DETAILED DESCRIPTION OF THE INVENTIONS

The following definitions of the general terms used in the present description apply irrespective of whether the terms in question appear alone or in combination.

As used herein, the term "lower alkyl" denotes a straight- or branched-chain hydrocarbon group containing from 1-8 carbon atoms, for example, methyl, ethyl, propyl, isopropyl, n-butyl, i-butyl, t-butyl and the like. Preferred lower alkyl groups are groups with 1-4 carbon atoms.

The term "lower alkyl substituted by halogen" denotes an alkyl group as defined above, wherein at least one hydrogen atom is replaced by halogen, for example —$CF_3$, —$CHF_2$, —$CH_2F$, —$CH_2CF_3$, —$CH_2CH_2CF_3$, —$CH_2CF_2CF_3$ and the like. Preferred lower alkyl substituted by halogen groups are groups having 1-4 carbon atoms.

The term "halogen" denotes chlorine, iodine, fluorine and bromine.

The term "aryl" denotes a cyclic aromatic hydrocarbon radical consisting of one or more fused rings containing 6-14 carbon atoms in which at least one ring is aromatic in nature, for example phenyl, benzyl, naphthyl or indanyl. Preferred is the phenyl group.

The term "heteroaryl" denotes a cyclic aromatic radical consisting of one or more fused rings containing 5-14 ring atoms, preferably containing 5-10 ring atoms, in which at least one ring is aromatic in nature, and which contains at least one heteroatom, selected from N, O and S, for example quinoxalinyl, dihydroisoquinolinyl, pyrazinyl, pyridazinyl, pyrazolyl, pyridinyl, pyridyl, pyrimidinyl, oxadiazolyl, triazolyl, [1,3,4]oxadiazolyl, tetrazolyl, thiazolyl, thiadiazolyl, thienyl, furyl, imidazolyl, or benzofuranyl. Preferred heteroaryl group is pyridinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

One embodiment of the invention provides compounds of formula I where n and m are each 1. Particularly, such compounds are those, wherein $Ar^1$ and $Ar^2$ are both pyridinyl groups, for example the following compounds:
4-{(3S,4R)-3-(4-chloro-phenyl)-4-[1-((S)-5-chloro-pyridin-2-yloxy)-ethyl]-pyrrolidine-1-carbonyl}-3,4,5,6-tetrahydro-2H-[1,2']bipyridinyl-5'-carbonitrile;

{(3 S,4R)-3-(4-chloro-phenyl)-4-[1-((S)-5-chloro-pyridin-2-yloxy)-ethyl]-pyrrolidin-1-yl}-(5'-trifluoromethyl-3,4,5,6-tetrahydro-2H-[1,2']bipyridinyl-4-yl)-methanone;
1-(4-{(3S,4R)-3-(4-chloro-phenyl)-4-[1-((S)-5-chloro-pyridin-2-yloxy)-ethyl]-pyrrolidine-1-carbonyl}-3,4,5,6-tetrahydro-2H-[1,2']bipyridinyl-5'-yl)-ethanone;
4-{(3S,4R)-3-(4-chloro-phenyl)-4-[1-((S)-5-chloro-pyridin-2-yloxy)-ethyl]-pyrrolidine-1-carbonyl}-3,4,5,6-tetrahydro-2H-[1,2']bipyridinyl-4'-carbonitrile;
{(3 S,4R)-3-(4-chloro-phenyl)-4-[1-((S)-5-chloro-pyridin-2-yloxy)-ethyl]-pyrrolidin-1-yl}-(5'-methoxy-3,4,5,6-tetrahydro-2H-[1,2']bipyridinyl-4-yl)-methanone;
{(3 S,4R)-3-(4-chloro-phenyl)-4-[1-((S)-5-chloro-pyridin-2-yloxy)-ethyl]-pyrrolidin-1-yl}-(6'-methoxy-3,4,5,6-tetrahydro-2H-[1,3']bipyridinyl-4-yl)-methanone; and
4-[(3R,4S)-3-[1-((S)-5-chloro-pyridin-2-yloxy)-ethyl]-4-(3,4-difluoro-phenyl)-pyrrolidine-1-carbonyl]-3,4,5,6-tetrahydro-2H-[1,2']bipyridinyl-5'-carbonitrile.

Another embodiment provides compounds, wherein $Ar^1$ is a pyridinyl group and $R^2$ is phenyl, for example
1-[4-(4-{(3 S,4R)-3-(4-chloro-phenyl)-4-[1-((S)-5-chloro-pyridin-2-yloxy)-ethyl]-pyrrolidine-1-carbonyl}-piperidin-1-yl)-phenyl]-ethanone.

A further embodiment provides compounds, wherein $Ar^1$ is a pyridinyl group and $R^2$ is a pyridazine group, for example:
6-(4-{(3 S,4R)-3-(4-chloro-phenyl)-4-[1-((S)-5-chloro-pyridin-2-yloxy)-ethyl]-pyrrolidine-1-carbonyl}-piperidin-1-yl)-pyridazine-3-carbonitrile and
6-(4-{(3S,4R)-3-(4-chloro-phenyl)-4-[1-((S)-5-fluoro-pyridin-2-yloxy)-ethyl]-pyrrolidine-1-carbonyl}-piperidin-1-yl)-pyridazine-3-carbonitrile.

The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process described below, which process comprises
a) coupling a compound of formula

VII

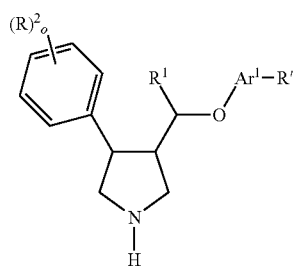

with a suitable acid chloride or carboxylic acid of formula

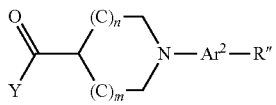

XIII wherein Y is halogen or hydroxy,
to obtain a compound of formula

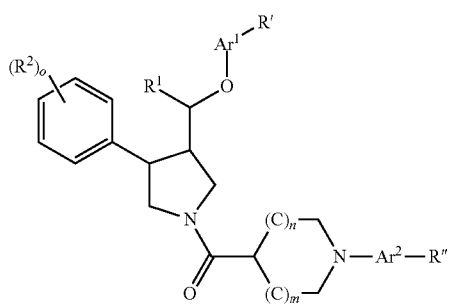

I wherein the substituents R¹, R², R', R", Ar¹, Ar² and the definitions o, n and m are described above,
b) reacting a compound of formula

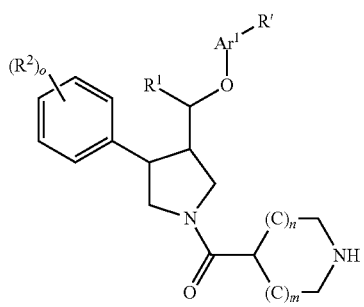

VIII with a compound of formula

R"—Ar²—Z wherein Z is halogen,
to obtain a compound of formula

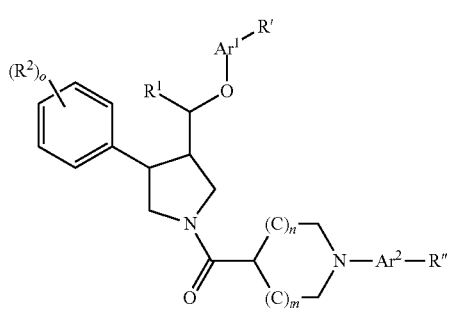

I wherein the substituents R¹, R², R', R", Ar¹, Ar² and the definitions o, n and m are described above, or, if desired, converting the compounds obtained into pharmaceutically acceptable acid addition salts.

The preparation of compounds of formula I is further described in more detail in schemes I-V and in examples 1-21.

Abbreviations:
$CH_2Cl_2$: dichloromethane;
DMAP: dimethylaminopyridine;
HOBt: 1-hydroxy-benzotriazol hydrat;
EDC: 1-(3-dimethylaminopropyl)-3-ethylcarbodiimide hydrochloride;
$Et_3N$: triethylamine;
EtOAc: ethyl acetate;
H: hexane;
RT: room temperature;
$PPh_3$: triphenylphosphine;
DBAD: di-tert-butyl azodicarboxylate General scheme I

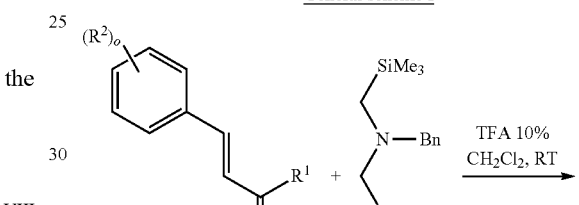

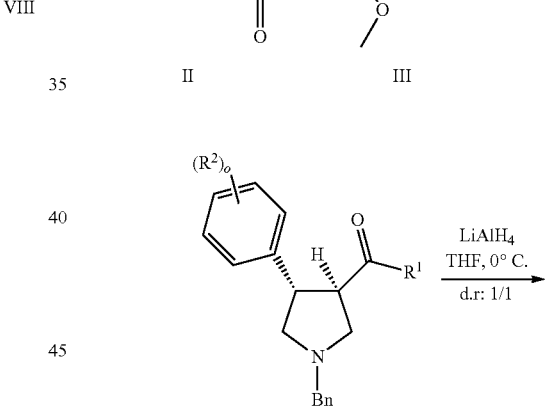

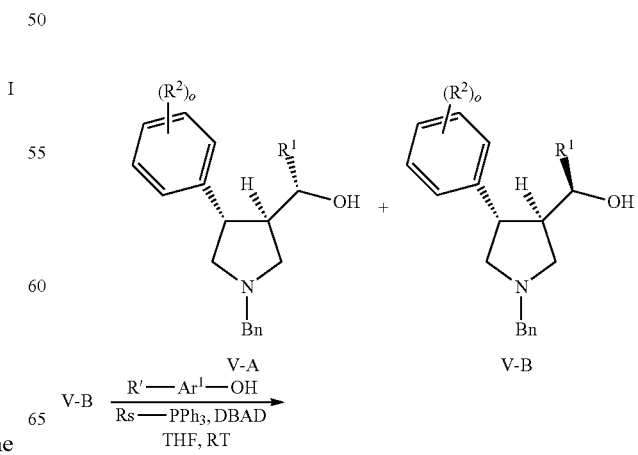

-continued

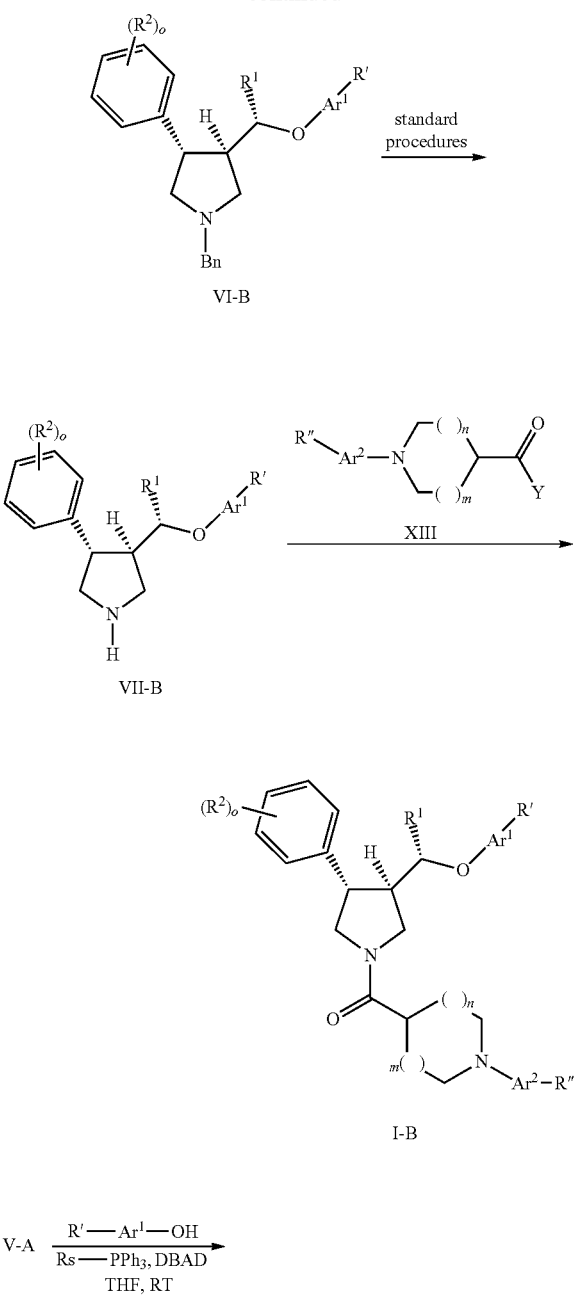

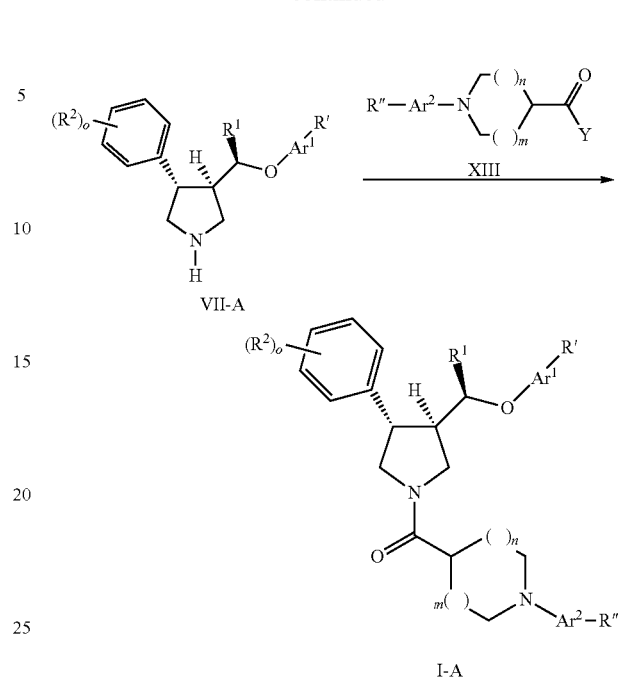

wherein Y is halogen or hydroxy, $R^1$ a lower alkyl and the other definitions are as described above.

The 3,4-disubstituted pyrrolidines IV are prepared via a stereo specific 1,3-dipolar cycloaddition between substituted (E)-4-phenyl-but-3-en-2-one derivative II and the azomethine glide generated in situ from the N-(methoxymethyl)-N-(phenylmethyl)-N-(trimethylsilyl)methylamine III in the presence of a catalytic amount of acid, such as TFA. Reduction of the acetyl moiety using standard conditions for example $LiAlH_4$ yields the two diastereoisomers V-A and V-B which are subsequently separated by column chromatography. Each of the diastereoisomers is then separately converted to the final derivatives I-A and I-B in the same manner. For instance V-B is subjected to a standard Mitsunobu reaction with for example a phenol, pyridin-ol, pyrimidin-ol to give the aryl-ether VI-B. Selective N-debenzylation is then carried out using several known procedures which are compatible with the substitution patterns of the aromatic rings to afford VII-B. Final derivatives I-B are prepared via a coupling with a suitable acid chloride or carboxylic acid XIII using known methods, wherein Y is hydroxy or halogen, $R^1$ a methyl moiety and the other definitions are as described above.

General scheme II

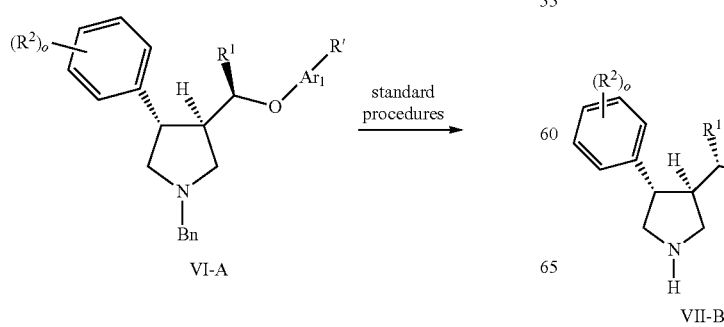

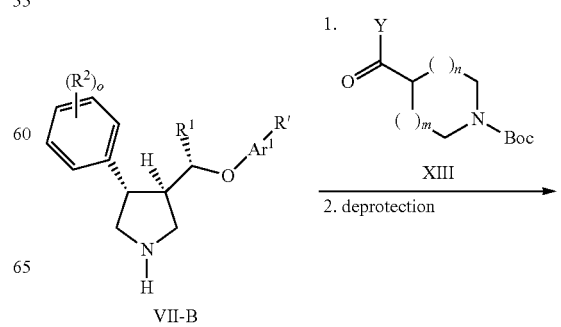

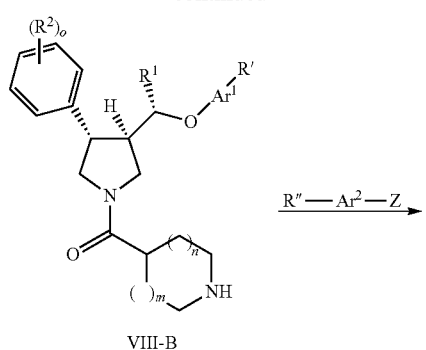

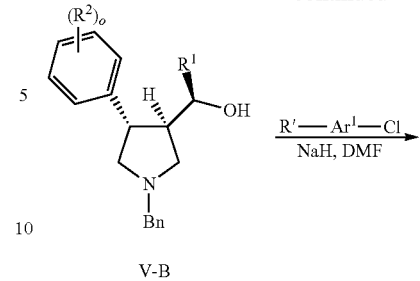

Alternatively the pyrrolidine VII-B can undergo a coupling with a carboxylic acid derivative which after selective Boc deprotection generated the intermediate VIII-B. Final derivatives I-B are prepared via a coupling with R"—Ar²—Z XIII using well known reactions and procedures (e.g. nucleophilic aromatic substitution, Buchwald coupling), wherein Z is halogen and the other definitions are as described above.

In the same manner, the diastereomer VII-A can be converted to final derivatives I-A

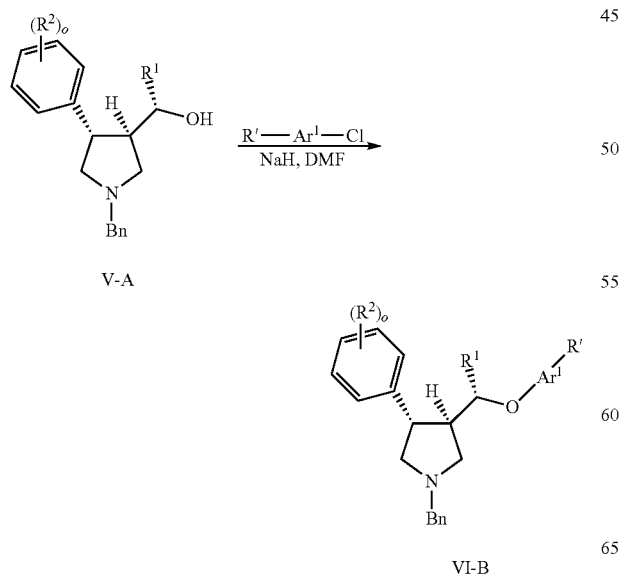

Alternatively to the Mitsunobu reaction shown scheme I, derivatives V-A and V-B can used in a nucleophilic aromatic substitution reaction when the Ar moiety is a o-pyridinyl or a o-pyrimidinyl to yield respectively VI-B and VI-A.

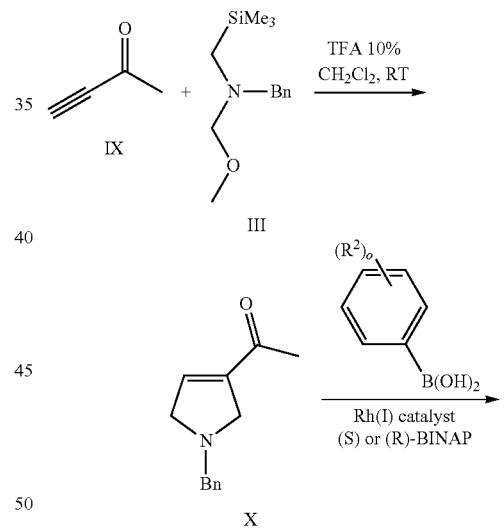

An alternative method for the preparation of intermediates IV (with $R^1$ is Me) is highlighted scheme 4. A 1,3-dipolar cycloaddition between the commercially available but-3-yn-2-one 1× and the azomethine glide generated in situ from the N-(methoxymethyl)-N-(phenylmethyl)-N-(trimethylsilyl)methylamine III in the presence of a catalytic amount of acid, such as TFA afforded the dihydropyrrole derivative X. A 1,4-addition of a boronic acid catalysed by a Rh(I) catalyst such as the Rhacetylacetonatbis(ethylene) in a presence of a chiral phosphine ligand such as the (R) or (S)-BINAP afforded the optically enriched disubstituted pyrrolidine IV. Similar Rh-catalysed asymmetric 1,4-arylation have been reported earlier (*Tet. Lett.*, 2004, 45(16), 3265)

General scheme V

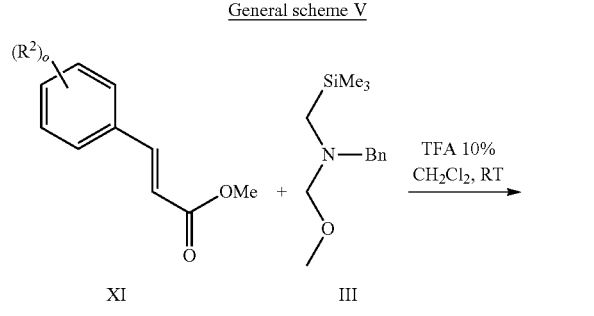

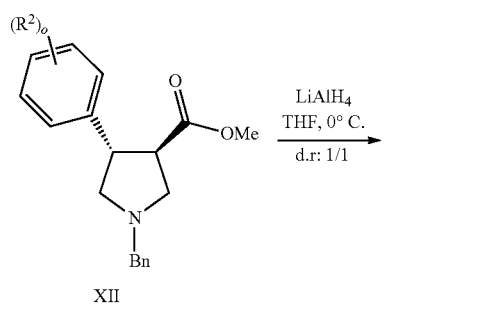

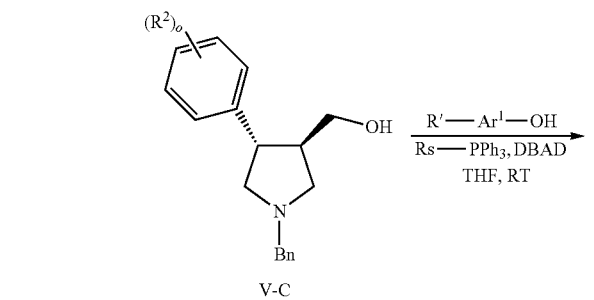

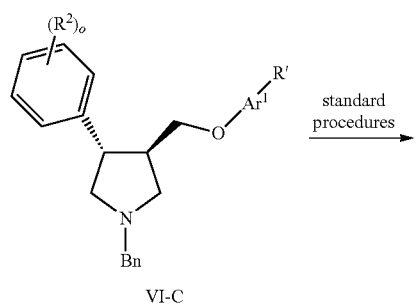

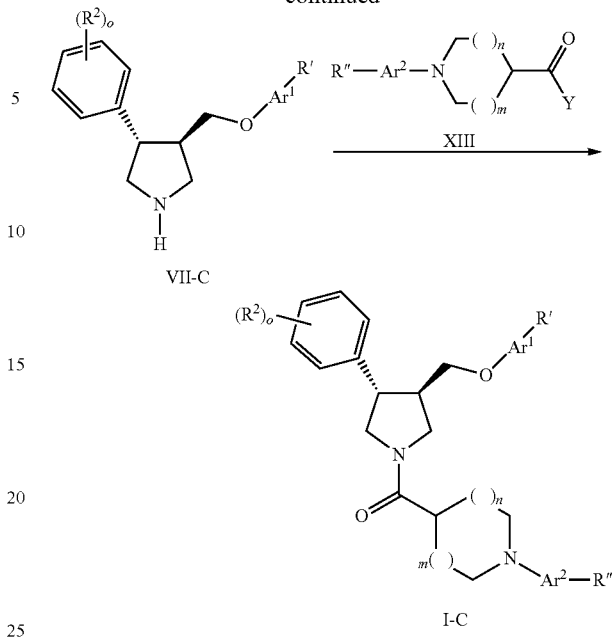

The derivatives of the type I-C with R1 equal H where prepared via the following route (scheme 5). The 3,4-disubstituted pyrrolidines XII were prepared via a stereo specific 1,3-dipolar cycloaddition between the (E)-3-substituted phenyl-acrylic acid ethyl ester derivatives XI and the azomethine glide generated in situ from the N-(methoxymethyl)-N-(phenylmethyl)-N-(trimethylsilyl)methylamine III in the presence of a catalytic amount of acid, such as TFA. Reduction of the ester moiety using standard conditions for example LiAlH$_4$ yielded the primary alcohol V-C. Standard Mitsunobu reaction with for example a phenol, pyridin-ol, pyrimidin-ol gave the aryl-ether VI-C. Selective N-debenzylation was then carried out using several known procedures which are compatible with the substitution patterns of the aromatic rings to afford VII-C. Final derivatives I—C were obtained via a coupling with a suitable acid chloride or carboxylic acide XIII using known methods.

EXPERIMENTAL PROCEDURES

As mentioned earlier, the compounds of formula I and their pharmaceutically acceptable addition salts possess valuable pharmacological properties. Compounds of the present invention are antagonists of neurokinin 3 (NK-3) receptors. The compounds were investigated in accordance with the tests given hereinafter.
Experimental Procedure
The compounds were investigated in accordance with the tests given hereinafter.
[$^3$H]SR142801 Competition Binding Assay
hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM MnCl$_2$, 1 μM phosphoramidon, 0.1% BSA binding buffer at pH 7.4 to a final assay concentration of 5 μg protein/well. For inhibition experiments, membranes were incubated with [$^3$H]

SR142801 at a concentration equal to $K_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Can berra Packard S. A., Zürich, Switzerland) and shaking for 1 h. Inhibition curves were fitted according to the Hill equation: $y=1+(x/IC_{50})^{nH}$, where $n_H$=slope factor using Excel-fit 4 software (Microsoft). $IC_{50}$ values were derived from the inhibition curve and the affinity constant ($K_i$) values were calculated using the Cheng-Prussoff equation $K_i=IC_{50}/(1+[L]/K_D)$ where [L] is the concentration of radioligand and $K_D$ is its dissociation constant at the receptor, derived from the saturation isotherm. All experiments were performed in duplicate and the mean±standard error (SEM) of the individual $K_i$ values was calculated.

The results of compounds with a good hNK-3 receptor affinity are shown in the following table 1.

TABLE 1

| Example | Ki (nM) |
|---------|---------|
| 1 | 0.4 |
| 2 | 1.9 |
| 3 | 2.1 |
| 4 | 0.8 |
| 5 | 0.4 |
| 6 | 0.5 |
| 7 | 1.2 |
| 8 | 1.3 |
| 9 | 0.5 |
| 10 | 6.1 |
| 11 | 0.5 |
| 12 | 2.1 |
| 13 | 0.7 |
| 14 | 1.2 |
| 15 | 0.5 |
| 16 | 0.8 |
| 17 | 1.5 |
| 18 | 3.1 |
| 19 | 1.2 |
| 20 | 0.9 |
| 21 | 2.8 |

The invention also provides pharmaceutical compositions containing compounds of formula I as well as their pharmaceutically acceptable acid addition salts and a pharmaceutically acceptable carrier. The pharmaceutical Compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compositions contain compounds of formula I and/or their pharmaceutically acceptable acid addition salts and pharmaceutically inert, inorganic or organic excipients for the production of tablets, coated tablets, dragees and hard gelatin capsules. Lactose, corn starch or derivatives thereof, talc, stearic acid or its salts etc can be used as such excipients e.g. for tablets, dragées and hard gelatin capsules.

Suitable excipients for soft gelatin capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

Example A

Tablets of the following composition are manufactured in the usual manner:

| | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

| | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelantine capsules.

Example C

Suppositories of the following composition are manufactured:

| | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following Examples illustrate the present invention without limiting it. All temperatures are given in degrees Celsius.

General Procedure I: Amid Coupling Between a Pyrrolidine VII and a Carboxylic Acid XIII To a stirred solution of a carboxylic acid derivative (commercially available or known in the literature or described hereinafter) (1 mmol) in 10 mL of $CH_2Cl_2$ was added (1.3 mmol) of EDC, (1.3 mmol) of HOBt and $Et_3N$ (1.3 mmol). After one hour at RT, was added a pyrrolidine intermediate of general formula (VII). The mixture was stirred at RT over night and then poured onto water and extracted with $CH_2Cl_2$. The combined organic phases were dried over $Na_2SO_4$ and concentrated under vacuo. Flash chromatography or preparative HPLC afforded the title compound.

General Procedure II: Aromatic Nucleophilic Substitution

To a stirred solution of an amine of type VIII (1 mmol) in DMF (5 mL) was added $EtNiPr_2$ (1.5 mmol) and a substituted chloropyridine, chloropyrimidine, or chloropyridazine (1.3 mmol). The reaction mixture was heated at 60 until completion (reaction monitored by TLC or LCMS). The reaction mixture was concentrated under vacuo, taken up in EtOAc and washed with $H_2O$ several times. The organic phase was dried over $Na_2SO_4$, concentrated under vacuo and then purified by preparative HPLC or column chromatography to yield the title product.

Pyrrolidine Intermediates of Formula VII-B

Pyrrolidine VII-B-1

5-Chloro-2-{(S)-1-[(3R,4S)-4-(4-chloro-phenyl)-pyrrolidin-3-yl]ethoxy}-pyridine

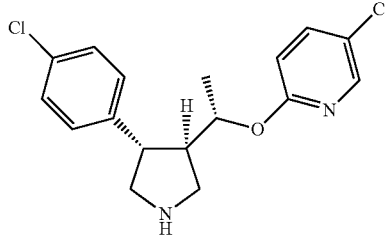

VII-B-1 a)-(1-Benzyl-2,5-dihydro-1H-pyrrol-3-yl)-ethanone

To a solution of N-(methoxymethyl)-N-(phenylmethyl)-N-(trimethylsilyl)methylamine (9.76 g, 0.041 mol) in $CH_2Cl_2$ (40 mL) at 0° C., was added dropwise over a 5 minutes period but-3-yn-2-one (2.0 g, 0.029 mol) followed by trifluoroacetic acid (0.22 mL, 0.003 mol) (very exothermic reaction). The ice bath was removed after 30 minutes, and the solution was stirred at 25° C. for an additional 2 h. It was then concentrated and purification by flash chromatography ($SiO_2$, EtOAc/Heptane 1:1) afforded 2.90 g (49%) of the title compound as a yellow oil. ES-MS m/e: 202.2 (M+H$^+$).

b) 1-[(3R,4 S)-1-Benzyl-4-(4-chloro-phenyl)-pyrrolidin-3-yl]-ethanone (IV-1)

A two necked flask was charged under argon with rhodium (acac)bis ethylene (45 mg, 0.05 eq.), (R)-BINAP (110 mg, 0.05 eq.) and 4-chloro-phenylboronic acid (1.20 g, 2.2 eq.). 100 mL of MeOH and 10 mL of $H_2O$ were added followed by 1-(1-benzyl-2,5-dihydro-1H-pyrrol-3-yl)-ethanone (0.70 g). The reaction mixture was heated at 55° C. for 8 hours, cooled down to RT and concentrated under vacuo. Purification by flash chromatography ($SiO_2$, EtOAc/Heptane 2/1) afforded 0.36 g (33%) of the title product as a light yellow oil. ES-MS m/e: 314.0 (M+H$^+$).

c) (S)-1-[(3R,4S)-1-Benzyl-4-(4-chloro-phenyl)-pyrrolidin-3-yl]-ethanol (V-A-1) and (R)-1-[(3R,4 S)-1-Benzyl-4-(4-chloro-phenyl)-pyrrolidin-3-yl]-ethanol (V-B-1)

To a solution of 1-[(3R,4S)-1-benzyl-4-(4-chloro-phenyl)-pyrrolidin-3-yl]-ethanone (0.52 g, 1.65 mmol) in THF (20 mL) at 0° C. were added portion wise $LiAlH_4$ (55 mg, 1.45 mmol). Stirring was continued for one hour, and the reaction mixture was carefully quenched by addition of aq. $NH_4Cl$, concentrated under vacuo and the product extracted with EtOAC. The combined organic phases were dried on $Na_2SO_4$ and concentrated under vacuo. The two diastereoisomers were separated by column chromatography ($SiO_2$, EtOAc/H, 1:1) to yield (R)-1-[(3R,4S)-1-benzyl-4-(4-chloro-phenyl)-pyrrolidin-3-yl]-ethanol (V-B-1) 0.24 g (46%) as a white solid ES-MS m/e: 316.1 (M+H$^+$) and (S)-1-[(3R,4S)-1-benzyl-4-(4-chloro-phenyl)-pyrrolidin-3-yl]-ethanol (V-A-1) 0.25 g (47%) as a white solid ES-MS m/e: 316.1 (M+H$^+$).

d) 2-{(S)-1-[(3R,4S)-1-Benzyl-4-(4-chloro-phenyl)-pyrrolidin-3-yl]-ethoxy}-5-chloro-pyridine (VI-B-1)

To a suspension of $PPh_3$ ($PPh_3$ polymer bound, 3 mmol $PPh_3$/g resin) (0.44 g, 1.69 mmol) in THF (50 mL) at 0° C. were added 5-chloro-pyridin-2-ol (0.15 g, 1.15 mmol) and then DBAD (0.28 g, 1.23 mmol). After 5 minutes was added (R)-1-[(3R,4S)-1-benzyl-4-(4-chloro-phenyl)-pyrrolidin-3-yl]-ethanol (0.25 g, 0.79 mmol). The reaction mixture was stirred over night at RT, filtered on celite and concentrated under vacuo. Extraction with EtOAc/aq.NaOH 1M, followed by column chromatography ($SiO_2$, EtOAc/H, 1:3) yielded 0.22 g (65%) of the title compound as a colorless oil. ES-MS m/e: 427.8 (M+H$^+$).

e) 5-Chloro-2-{(S)-1-[(3R,4S)-4-(4-chloro-phenyl)-pyrrolidin-3-yl]-ethoxy}-pyridine(VII-B-1)

To a solution of 2-{(S)-1-[(3R,4S)-1-benzyl-4-(4-chloro-phenyl)-pyrrolidin-3-yl]-ethoxy}-5-chloro-pyridine 220 mg (0.51 mmol) dissolved in toluene (5 mL) were added 0.17 mL (1.53 mmol) of 1-chloroethyl chloroformate and 0.27 mL (1.53 mmol) of Hunig's base. The reaction mixture was heated at 100° C. for one hour. After cooling down to RT, volatiles were removed under vacuo and the crude was dissolved in MeOH (10 mL). The reaction mixture was heated at 85° C. for 30 minutes and after cooling down to RT, volatiles were removed under vacuo and the residue was directly purified on column chromatography ($SiO_2$, $CH_2Cl_2$/MeOH 9:1) yielded 110 mg (62%) of the title compound as a light yellow oil. ES-MS m/e: 337.1 (M+H$^+$).

Pyrrolidine VII-B-2

2-{(S)-1-[(3R,4S)-4-(4-Chloro-phenyl)-pyrrolidin-3-yl]ethoxy}-5-fluoro-pyridine

VII-B-2 a) 2-{(S)-1-[(3R,4S)-1-Benzyl-4-(4-chloro-phenyl)-pyrrolidin-3-yl]-ethoxy}-5-fluoro-pyridine (VI-B-2)

To a suspension of PPh₃ (PPh₃ polymer bound, 3 mmol PPh₃/g resin) (0.914 g, 2.74 mmol) in THF (15 mL) at 0° C. were added 5-fluoro-pyridin-2-ol (0.215 g, 1.90 mmol) and then DBAD (0.47 g, 2.02 mmol). After 5 minutes was added (R)-1-[(3R,4S)-1-benzyl-4-(4-chloro-phenyl)-pyrrolidin-3-yl]-ethanol (0.40 g, 1.26 mmol; described herein above). The reaction mixture was stirred over night at RT, filtered on celite and concentrated under vacuo. Extraction with EtOAc/aq.NaOH 1M, followed by column chromatography (SiO₂, EtOAc/H, 1:3) yielded 0.315 g (44%) of the title compound as a colorless oil. ES-MS m/e: 411.2 (M+H⁺).

b) 2-{(S)-1-[(3R,4S)-4-(4-Chloro-phenyl)-pyrrolidin-3-yl]-ethoxy}-5-fluoro-pyridine (VII-B-2)

To a solution of 2-{(S)-1-[(3R,4S)-1-benzyl-4-(4-chloro-phenyl)-pyrrolidin-3-yl]-ethoxy}-5-fluoro-pyridine 310 mg (0.75 mmol) dissolved in toluene (5 mL) were added 0.10 mL (0.98 mmol) of 1-chloroethyl chloroformate and 0.17 mL (0.98 mmol) of Hunig's base. The reaction mixture was heated at 100° C. for one hour. After cooling down to RT, volatiles were removed under vacuo and the crude was dissolved in MeOH (10 mL). The reaction mixture was heated at 85° C. for 30 minutes and after cooling down to RT, volatiles were removed under vacuo and the residue was directly purified on column chromatography (SiO₂, CH₂Cl₂/MeOH 9:1) yielded 230 mg (85%) of the title compound as a light yellow oil. ES-MS m/e: 321.3 (M+H⁺).

Pyrrolidine VII-B-3

5-Chloro-2-{(S)-1-[(3R,4S)-4-(3,4-difluoro-phenyl)-pyrrolidin-3-yl]-ethoxy}-pyridine

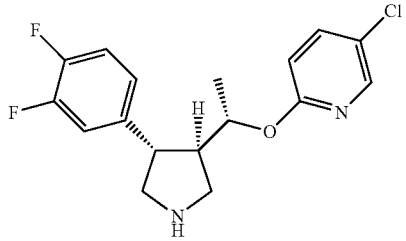

VII-B-3 a) 1-[(3R,4S)-1-Benzyl-4-(3,4-difluoro-phenyl)-pyrrolidin-3-yl]-ethanone (IV-3)

A two necked flask was charged under argon with rhodium (acac)bis ethylene (0.239 g, 0.05 eq.), (R)-BINAP (0.575 g, 0.05 eq.) and 3,4-difluoro-phenylboronic acid (7.3 g, 2.5 eq.). 400 mL of MeOH and 40 mL of H₂O were added followed by 1-(1-benzyl-2,5-dihydro-1H-pyrrol-3-yl)-ethanone (3.72 g). The reaction mixture was heated at 55° C. for 8 hours, cooled down to RT and concentrated under vacuo. Purification by flash chromatography (SiO₂, EtOAc/Heptane 2/1) afforded 2.31 g (40%) of the title product as a light yellow oil. ES-MS m/e: 316.1 (M+H⁺).

b) (S)-1-[(3R,4S)-1-Benzyl-4-(3,4-difluoro-phenyl)-pyrrolidin-3-yl]-ethanol (V-A-3) and (R)-1-[(3R,4S)-1-Benzyl-4-(3,4-difluoro-phenyl)-pyrrolidin-3-yl]-ethanol (V-B-3)

To a solution of 1-[(3R,4S)-1-benzyl-4-(3,4-difluoro-phenyl)-pyrrolidin-3-yl]-ethanone (2.31 g, 7.32 mmol) in THF (80 mL) at 0° C. were added portion wise LiAlH₄ (0.245 g, 6.44 mmol). Stirring was continued for one hour, and the reaction mixture was carefully quenched by addition of aq. NH₄Cl, concentrated under vacuo and the product extracted with EtOAC. The combined organic phases were dried on Na₂SO₄ and concentrated under vacuo. The two diastereoisomers were separated by column chromatography (SiO₂, EtOAc/H, 1:1) to yield (R)-1-[(3R,4S)-1-benzyl-4-(3,4-difluoro-phenyl)-pyrrolidin-3-yl]-ethanol (V-B-3) 0.98 g (42%) as a white solid ES-MS m/e: 318.1 (M+H⁺) and (S)-1-[(3R,4S)-1-benzyl-4-(3,4-difluoro-phenyl)-pyrrolidin-3-yl]-ethanol (V-A-3) 0.86 g (37%) as a white solid ES-MS m/e: 318.1 (M+H⁺).

c) 2-{(S)-1-[(3R,4S)-1-Benzyl-4-(3,4-difluoro-phenyl)-pyrrolidin-3-yl]-ethoxy}-5-chloro-pyridine (VI-B-3)

To a suspension of PPh₃ (PPh₃ polymer bound, 3 mmol PPh₃/g resin) (1.78 g, 6.79 mmol) in THF (20 mL) at 0° C. were added 5-chloro-pyridin-2-ol (0.60 g, 4.63 mmol) and then DBAD (1.14 g, 4.95 mmol). After 5 minutes was added (R)-1-[(3R,4S)-1-benzyl-4-(3,4-difluoro-phenyl)-pyrrolidin-3-yl]-ethanol (0.98 g, 3.09 mmol). The reaction mixture was stirred over night at RT, filtered on celite and concentrated under vacuo. Extraction with EtOAc/aq.NaOH 1M, followed by column chromatography (SiO₂, EtOAc/H, 1:3) yielded 0.917 g (69%) of the title compound as a colorless oil. ES-MS m/e: 429.2 (M+H⁺).

d) 5-Chloro-2-{(S)-1-[(3R,4S)-4-(3,4-difluoro-phenyl)-pyrrolidin-3-yl]-ethoxy}-pyridine (VII-B-3)

To a solution of 2-{(S)-1-[(3R,4S)-1-benzyl-4-(3,4-difluoro-phenyl)-pyrrolidin-3-yl]-ethoxy}-5-chloro-pyridine 917 mg (2.13 mmol) dissolved in toluene (20 mL) were added 0.69 mL (6.39 mmol) of 1-chloroethyl chloroformate and 1.09 mL (6.39 mL) of Hunig's base. The reaction mixture was heated at 100° C. for one hour. After cooling down to RT, volatiles were removed under vacuo and the crude was dissolved in MeOH (20 mL). The reaction mixture was heated at 85° C. for 30 minutes and after cooling down to RT, volatiles were removed under vacuo and the residue was directly purified on column chromatography (SiO₂, CH₂Cl₂/MeOH 9:1) yielded 464 mg (64%) of the title compound as a light yellow oil. ES-MS m/e: 339.1 (M+H⁺).

Pyrrolidine VII-B-4

6-{(S)-1-[(3R,4S)-4-(3,4-Difluoro-phenyl)-pyrrolidin-3-yl]ethoxy}-nicotinonitrile

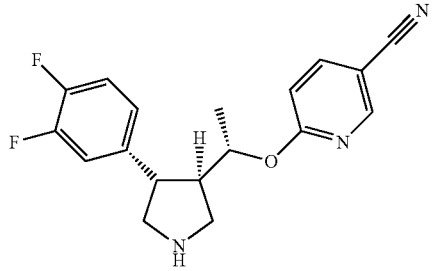

VII-B-4 a) 6-{(S)-1-[(3R,4S)-1-Benzyl-4-(3,4-difluoro-phenyl)-pyrrolidin-3-yl]-ethoxy}-nicotinonitrile (VI-B-4)

To a stirred solution of 84 mg (0.26 mmol) of (S)-1-[(3R,4S)-1-benzyl-4-(3,4-difluoro-phenyl)-pyrrolidin-3-yl]-ethanol in DMF (10 mL) was added NaH (19 mg, 0.40 mmol). The reaction mixture was stirred at RT for 30 minutes, and then at 50° C. for 20 minutes. A solution of 6-chloro-nicotinonitrile (45 mg, 0.32 mmol) in DMF (2 mL) was added dropwise and stirring was continued 3 hours at 50° C. The reaction mixture was concentrated under vacuo. Extraction with EtOAc/H₂O, followed by column chromatography (SiO₂, EtOAc/H, 1:3) yielded 66 mg (60%) of the title compound as a colorless oil. ES-MS m/e: 420.3 (M+H⁺).

b) 6-{(S)-1-[(3R,4S)-4-(3,4-Difluoro-phenyl)-pyrrolidin-3-yl]-ethoxy}-nicotinonitrile (VII-B-4)

To a solution of 6-{(S)-1-[(3R,4S)-1-benzyl-4-(3,4-difluoro-phenyl)-pyrrolidin-3-yl]-ethoxy}-nicotinonitrile 66 mg (0.16 mmol) dissolved in toluene (2 mL) were added 67 mg (0.47 mmol) of 1-chloroethyl chloroformate and 61 mg (0.47 mmol) of Hunig's base. The reaction mixture was heated at 100° C. for one hour. After cooling down to RT, volatiles were removed under vacuo and the crude was dissolved in MeOH (10 mL). The reaction mixture was heated at 85° C. for 30 minutes and after cooling down to RT, volatiles were removed under vacuo and the residue was directly purified on column chromatography (SiO$_2$, CH$_2$Cl$_2$/MeOH 9:1) yielded 45 mg (85%) of the title compound as a light yellow oil. ES-MS m/e: 330.3 (M+H$^+$).

Pyrrolidine Intermediates of Formula VIII-B

Pyrrolidine VIII-B-1

{(3S,4R)-3-(4-Chloro-phenyl)-4-[1-((S)-5-chloro-pyridin-2-yloxy)-ethyl]-pyrrolidin-1-yl}-piperidin-4-yl-methanone

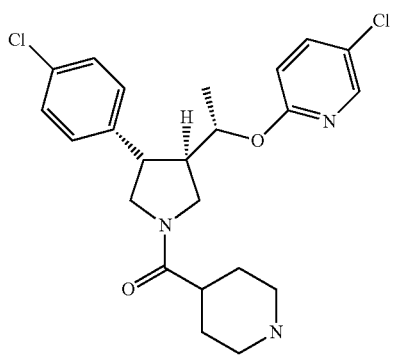

VIII-B-1

To a stirred solution of piperidine-1,4-dicarboxylic acid mono-tert-butyl ester (0.575 g, 2.51 mmol) in 10 mL of CH$_2$Cl$_2$ was added (0.48 g, 2.50 mmol) of EDC, (0.138 g, 2.50 mmol) of HOBt and Et$_3$N (0.67 mL, 4.81 mmol). After one hour at RT, was added 5-chloro-2-{(S)-1-[(3R,4S)-4-(4-chloro-phenyl)-pyrrolidin-3-yl]-ethoxy}-pyridine (VII-B-1), 0.72 g, 1.92 mmol). The mixture was stirred at RT over night and then poured onto water and extracted with CH$_2$Cl$_2$. The combined organic phases were dried over Na$_2$SO$_4$ and concentrated under vacuo. The crude residue was then dissolved in 20 mL of CH$_2$Cl$_2$ and 5 mL of TFA was added. After one hour at RT, the reaction was quenched by addition of aq. NaOH 1M (until ph=10) and the product was extracted with CH$_2$Cl$_2$. The combined organic phases were dried over Na$_2$SO$_4$ and concentrated under vacuo to yield 0.70 g (81%) of the title compound as a white foam. ES-MS m/e: 448.1 (M+H$^+$).

Pyrrolidine VIII-B-2

{(3S,4R)-3-(4-Chloro-phenyl)-4-[1-((S)-5-fluoro-pyridin-2-yloxy)-ethyl]-pyrrolidin-1-yl}-piperidin-4-yl-methanone

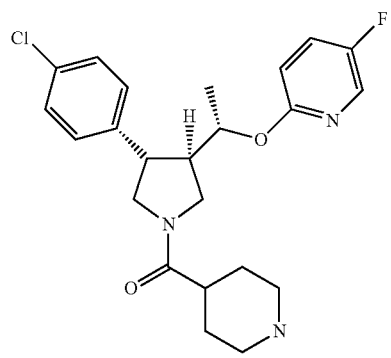

VIII-B-2

To a stirred solution of piperidine-1,4-dicarboxylic acid mono-tert-butyl ester (33 mg, 0.14 mmol) in 5 mL of CH$_2$Cl$_2$ was added (28 mg, 0.15 mmol) of EDC, (20 mg, 0.15 mmol) of HOBt and Et$_3$N (39 uL, 0.27 mmol). After one hour at RT, was added 2-{(S)-1-[(3R,4S)-4-(4-chloro-phenyl)-pyrrolidin-3-yl]-ethoxy}-5-fluoro-pyridine (VII-B-2), 40 mg, 0.11 mmol). The mixture was stirred at RT over night and then poured onto water and extracted with CH$_2$Cl$_2$. The combined organic phases were dried over Na$_2$SO$_4$ and concentrated under vacuo. The crude residue was then dissolved in 5 mL of CH$_2$Cl$_2$ and 1 mL of TFA was added. After one hour at RT, the reaction was quenched by addition of aq. NaOH 1M (until ph=10) and the product was extracted with CH$_2$Cl$_2$. The combined organic phases were dried over Na$_2$SO$_4$ and concentrated under vacuo to yield 39 mg (81%) of the title compound as a white foam. ES-MS m/e: 432.3 (M+H$^+$).

Carboxylic Acid XIII

Acid XIII-1

5'-Methoxy-3,4,5,6-tetrahydro-2H-[1,2']bipyridinyl-4-carboxylic acid

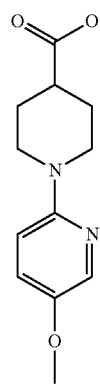

a) 5'-Methoxy-3,4,5,6-tetrahydro-2H-[1,2']bipyridinyl-4-carboxylic acid ethyl ester To a stirred solution of piperidine-4-carboxylic acid ethyl ester (0.52 g, 3.34 mmol) and 2-chloro-5-methoxy-pyridine in 10 mL of toluene was added (13 mg, 0.057 mmol) of Pd(II)

acetate, (17 mg, 0.027 mmol) of BINAP and tBuOK (0.44 g, 3.90 mmol). The mixture was heated at 120° C. for two hours, concentrated under vacuo and the residue was directly purified on column chromatography (SiO$_2$, EtOAc/Hept 1:2) yielding 0.17 g (24%) of the title compound as a light yellow oil. ES-MS m/e: 265.3 (M-41').

b)  5'-Methoxy-3,4,5,6-tetrahydro-2H-[1,2']bipyridinyl-4-carboxylic acid

To a solution of 5'-Methoxy-3,4,5,6-tetrahydro-2H-[1,2']bipyridinyl-4-carboxylic acid ethyl ester (0.17 g, 0.64 mmol) in 5 mL of THF/MeOH/H$_2$O (1/1/1) was added LiOH.H$_2$O (54 mg, 1.28 mmol). After 3 hours, the reaction was concentrated under vacuo, taken up in EtOAc, washed with aq. NH$_4$Cl. The organic phase was dried over Na$_2$SO$_4$, and concentrated under vacuo to yield 60 mg (39%) of the title product as a light brown solid. ES-MS m/e: 235.1 (M−H$^+$).

Acid XIII-2

1-(6-Methoxy-pyridazin-3-yl)-piperidine-4-carboxylic acid

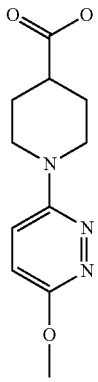

Using a similar procedure as for the preparation of XIII-1, using 3-chloro-6-methoxy-pyridazine was prepared 1-(6-methoxy-pyridazin-3-yl)-piperidine-4-carboxylic acid as a brown solid. ES-MS m/e: 236.3 (M−H$^+$).

Acid XIII-3

6'-Methoxy-3,4,5,6-tetrahydro-2H-[1,3']bipyridinyl-4-carboxylic acid

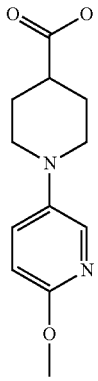

Using a similar procedure as for the preparation of XIII-1, using 5-chloro-2-methoxy-pyridine was prepared 6'-methoxy-3,4,5,6-tetrahydro-2H-[1,3']bipyridinyl-4-carboxylic acid as a brown solid. ES-MS m/e: 235.1 (M+H$^+$).

Acid XIII-4

1-(5-Methyl-[1,3,4]oxadiazol-2-yl)-piperidine-4-carboxylic acid

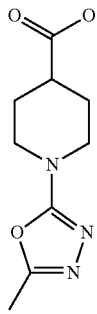

a) 1-Hydrazinocarbonyl-piperidine-4-carboxylic acid ethyl ester

A solution of triphosgene (9.44 g, 31.8 mmol) in THF (100 ml) was cooled to 0° C. and piperidine-4-carboxylic acid ethyl ester (10.0 g, 63.6 mmol) was added over 15 minutes while the temperature was maintained between 0-5° C. Then N,N-diisopropyl ethyl amine (33 ml, 191 mmol) was added over 60 minutes. The suspension was stirred for 18 h at rt. The suspension was filtered off and washed with THF (50 ml). The filtrate was transferred into a dropping funnel and added dropwise over 60 minutes to hydrazine monohydrate (9.3 ml, 191 mmol) at 5-10° C. The suspension was stirred for 3 h at 5° C. The reaction mixture was washed twice with brine (100 ml). The aq. layers were extracted with EtOAc (100 ml). The combined organic layers were dried over Na$_2$SO$_4$ and concentrated under vacuo to yield 13.4 g (98%) of the title product as a brown oil. ES-MS m/e: 216.3 (M+H$^+$).

b)  1-(5-Methyl-[1,3,4]oxadiazol-2-yl)-piperidine-4-carboxylic acid ethyl ester

To a solution of 1-hydrazinocarbonyl-piperidine-4-carboxylic acid ethyl ester (215 mg, 0.999 mmol) in THF (2 ml) was added acetic anhydride (188 µl, 2.00 mmol). After stirring for 5 minutes at rt phosphorus oxychloride (182 µl, 2.00 mmol) was added and the reaction mixture was stirred for 5 days at RT. The reaction mixture was added dropwise onto a 1 M solution of sodium carbonate (10 ml). The mixture was diluted with EtOAc (15 ml). The aq. layer was extracted with EtOAc (15 ml). The organic layers were washed with brine (15 ml) and dried over Na$_2$SO$_4$. A column chromatography (SiO$_2$, EtOAc/Hept 1/1 to Hept/MeOH 9/1) yielded 48 mg (20%) of the title product as a light brown oil. MS m/e: 240.3 [M+H]+ c)  1-(5-Methyl-[1,3,4]oxadiazol-2-yl)-piperidine-4-carboxylic acid

To a solution of 1-(5-methyl-[1,3,4]oxadiazol-2-yl)-piperidine-4-carboxylic acid ethyl ester (1.41 g, 5.89 mmol) in ethanol (5 ml) was added a 1 M solution of sodium hydroxide (5.9 ml, 5.9 mmol). The solution was stirred for 18 h at RT, and then acified by addition of a 1 M solution of hydrochloric acid (5.9 ml). The reaction mixture was concentrated in vacuo. After the addition of Na$_2$SO$_4$ the residue was suspended in THF (20 ml), filtered off and washed with THF and dried under vacuo. The title compound (0.72 g, 38%) was obtained as an off-white solid. MS m/e: 210.1 [M−H].

Example 1

4-{(3S,4R)-3-(4-Chloro-phenyl)-4-[1-((S)-5-chloro-pyridin-2-yloxy)-ethyl]-pyrrolidine-1-carbonyl}-3,4,5,6-tetrahydro-2H-[1,2']bipyridinyl-5'-carbonitrile

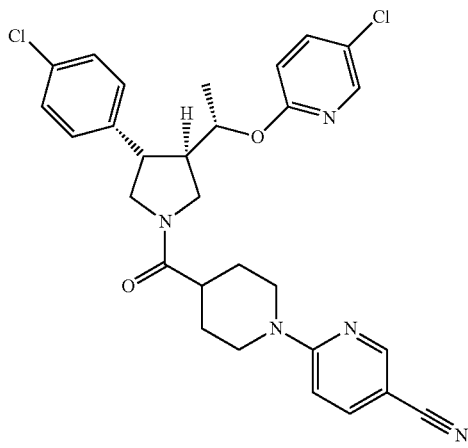

Amid coupling according to general procedure I:
Pyrrolidine intermediate: 5-Chloro-2-{(S)-1-[(3R,4S)-4-(4-chloro-phenyl)-pyrrolidin-3-yl]-ethoxy}-pyridine (VII-B-1)
Carboxylic acid: 5'-Cyano-3,4,5,6-tetrahydro-2H-[1,2]bipyridinyl-4-carboxylic acid (commercially available),
ES-MS m/e: 550.4 (M+H$^+$).

Example 2

{(3S,4R)-3-(4-Chloro-phenyl)-4-[1-((S)-5-chloro-pyridin-2-yloxy)-ethyl]-pyrrolidin-1-yl}-(1-pyrazin-2-yl-piperidin-4-yl)-methanone

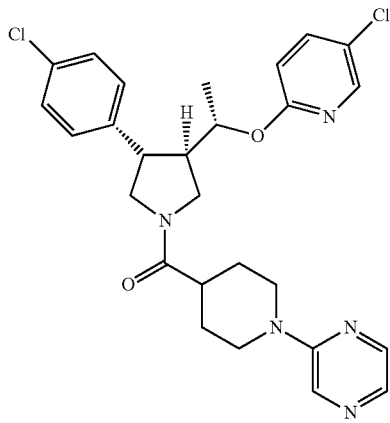

Amid coupling according to general procedure I:
Pyrrolidine intermediate: 5-Chloro-2-{(S)-1-[(3R,4S)-4-(4-chloro-phenyl)-pyrrolidin-3-yl]-ethoxy}-pyridine (VII-B-1)
Carboxylic acid: 1-Pyrazin-2-yl-piperidine-4-carboxylic acid (commercially available),
ES-MS m/e: 526.2 (M+H$^+$).

Example 3

{(3S,4R)-3-(4-Chloro-phenyl)-4-[1-((S)-5-chloro-pyridin-2-yloxy)-ethyl]-pyrrolidin-1-yl}-(1-pyrimidin-2-yl-piperidin-4-yl)-methanone

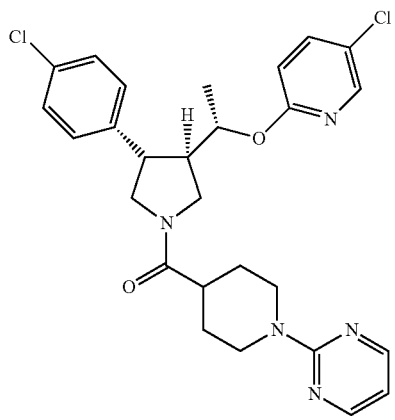

Amid coupling according to general procedure I:
Pyrrolidine intermediate: 5-Chloro-2-{(S)-1-[(3R,4S)-4-(4-chloro-phenyl)-pyrrolidin-3-yl]-ethoxy}-pyridine (VII-B-1)
Carboxylic acid: 1-Pyrimidin-2-yl-piperidine-4-carboxylic acid (commercially available),
ES-MS m/e: 526.2 (M+H$^+$).

Example 4

{(3S,4R)-3-(4-Chloro-phenyl)-4-[1-((S)-5-chloro-pyridin-2-yloxy)-ethyl]-pyrrolidin-1-yl}-(5'-trifluoromethyl-3,4,5,6-tetrahydro-2H-[1,2']bipyridinyl-4-yl)-methanone

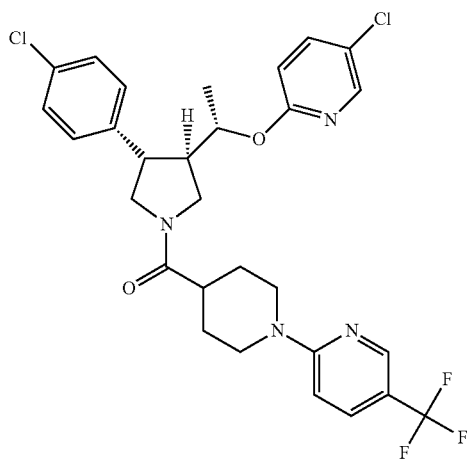

Amid coupling according to general procedure I:
Pyrrolidine intermediate: 5-Chloro-2-{(S)-1-[(3R,4S)-4-(4-chloro-phenyl)-pyrrolidin-3-yl]-ethoxy}-pyridine (VII-B-1)
Carboxylic acid: 5'-Trifluoromethyl-3,4,5,6-tetrahydro-2H-[1,2']bipyridinyl-4-carboxylic acid (commercially available),
ES-MS m/e: 593.2 (M+H$^+$).

Example 5

1-[4-(4-{(3S,4R)-3-(4-Chloro-phenyl)-4-[1-((S)-5-chloro-pyridin-2-yloxy)-ethyl]-pyrrolidine-1-carbonyl}-piperidin-1-yl)-phenyl]-ethanone

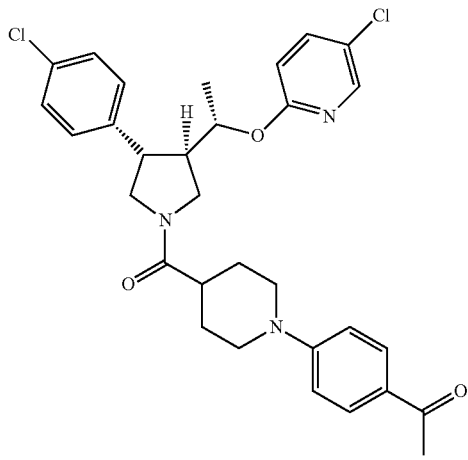

Amid coupling according to general procedure I:

Pyrrolidine intermediate: 5-Chloro-2-{(S)-1-[(3R,4S)-4-(4-chloro-phenyl)-pyrrolidin-3-yl]-ethoxy}-pyridine (VII-B-1)

Carboxylic acid: 1-(4-Acetyl-phenyl)-piperidine-4-carboxylic acid (commercially available), ES-MS m/e: 566.3 (M+H⁺).

Example 6

6-(4-{(3S,4R)-3-(4-Chloro-phenyl)-4-[1-((S)-5-chloro-pyridin-2-yloxy)-ethyl]-pyrrolidine-1-carbonyl}-piperidin-1-yl)-pyridazine-3-carbonitrile

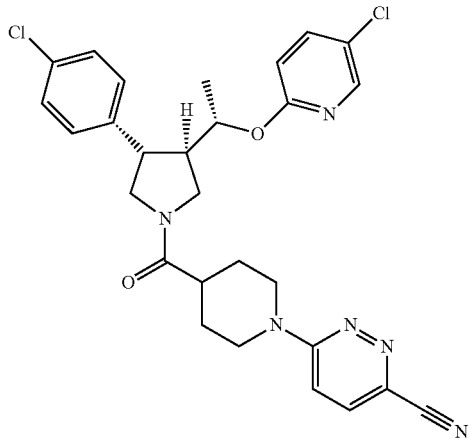

Coupling according to general procedure II:

Amine intermediate: {(3S,4R)-3-(4-Chloro-phenyl)-4-[1-((S)-5-chloro-pyridin-2-yloxy)-ethyl]pyrrolidin-1-yl}-piperidin-4-yl-methanone (VIII-B-1)

Heteroaryl: 6-Chloro-pyridazine-3-carbonitrile (commercially available),

ES-MS m/e: 551.3 (M+H⁺).

Example 7

4-{(3S,4R)-3-(4-Chloro-phenyl)-4-[1-((S)-5-fluoro-pyridin-2-yloxy)-ethyl]-pyrrolidine-1-carbonyl}-3,4,5,6-tetrahydro-2H-[1,2']bipyridinyl-5'-carbonitrile

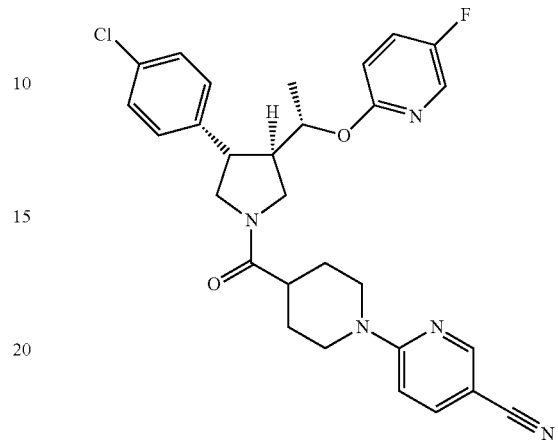

Amid coupling according to general procedure I:

Pyrrolidine intermediate: 2-{(S)-1-[(3R,4S)-4-(4-Chloro-phenyl)-pyrrolidin-3-yl]-ethoxy}-5-fluoro-pyridine (VII-B-2)

Carboxylic acid: 5'-Cyano-3,4,5,6-tetrahydro-2H-[1,2']bipyridinyl-4-carboxylic acid (commercially available), ES-MS m/e: 534.2 (M+H⁺).

Example 8

{(3S,4R)-3-(4-Chloro-phenyl)-4-[1-((S)-5-chloro-pyridin-2-yloxy)-ethyl]pyrrolidin-1-yl}-(1-pyrimidin-4-yl-piperidin-4-yl)-methanone

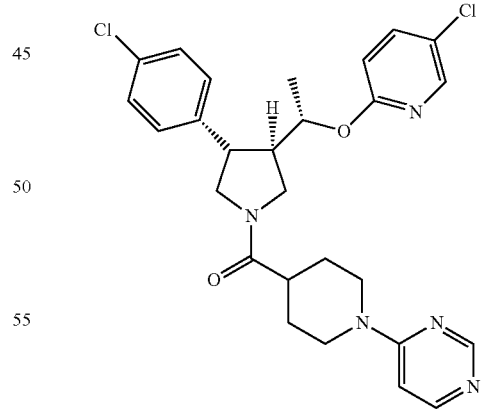

Coupling according to general procedure II:

Amine intermediate: {(3S,4R)-3-(4-Chloro-phenyl)-4-[1-((S)-5-chloro-pyridin-2-yloxy)-ethyl]pyrrolidin-1-yl}-piperidin-4-yl-methanone (VIII-B-1)

Heteroaryl: 4-Chloro-pyrimidine (commercially available),

ES-MS m/e: 526.2 (M+H⁺).

Example 9

1-(4-{(3S,4R)-3-(4-Chloro-phenyl)-4-[1-((S)-5-chloro-pyridin-2-yloxy)-ethyl]-pyrrolidine-1-carbonyl}-3,4,5,6-tetrahydro-2H-[1,2']bipyridinyl-5'-yl)-ethanone

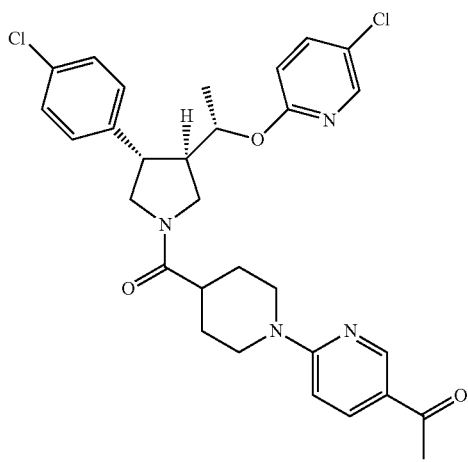 [SMILES: CC(=O)c1ccc(N2CCC(C(=O)N3C[C@H]([C@H](C)Oc4ccc(Cl)cn4)[C@@H](c4ccc(Cl)cc4)C3)CC2)nc1]

Coupling according to general procedure II:
Amine intermediate: {(3S,4R)-3-(4-Chloro-phenyl)-4-[1-((S)-5-chloro-pyridin-2-yloxy)-ethyl]-pyrrolidin-1-yl}-piperidin-4-yl-methanone (VIII-B-1)
Heteroaryl: 1-(6-Chloro-pyridin-3-yl)-ethanone (commercially available),
ES-MS m/e: 567.2 (M+H$^+$).

Example 10

4-{(3S,4R)-3-(4-Chloro-phenyl)-4-[1-((S)-5-chloro-pyridin-2-yloxy)-ethyl]-pyrrolidine-1-carbonyl}-3,4,5,6-tetrahydro-2H-[1,2']bipyridinyl-3'-carbonitrile

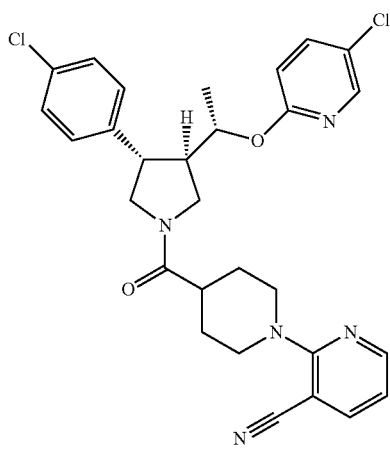 [SMILES: C[C@H](Oc1ccc(Cl)cn1)[C@H]1CN(C(=O)C2CCN(c3ncccc3C#N)CC2)C[C@@H]1c1ccc(Cl)cc1]

Coupling according to general procedure II:
Amine intermediate: {(3S,4R)-3-(4-Chloro-phenyl)-4-[1-((S)-5-chloro-pyridin-2-yloxy)-ethyl]-pyrrolidin-1-yl}-piperidin-4-yl-methanone (VIII-B-1)
Heteroaryl: 2-Chloro-nicotinonitrile (commercially available),
ES-MS m/e: 550.3 (M+H$^+$).

Example 11

4-{(3S,4R)-3-(4-Chloro-phenyl)-4-[1-((S)-5-chloro-pyridin-2-yloxy)-ethyl]-pyrrolidine-1-carbonyl}-3,4,5,6-tetrahydro-2H-[1,2']bipyridinyl-4'-carbonitrile

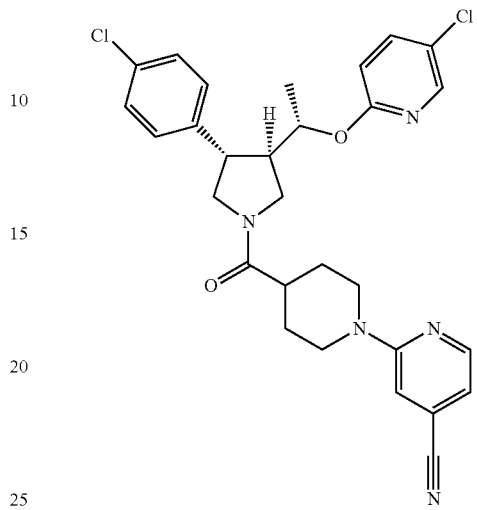

Coupling according to general procedure II:
Amine intermediate: {(3S,4R)-3-(4-Chloro-phenyl)-4-[1-((S)-5-chloro-pyridin-2-yloxy)-ethyl]-pyrrolidin-1-yl}-piperidin-4-yl-methanone (VIII-B-1)
Heteroaryl: 2-Chloro-isonicotinonitrile (commercially available),
ES-MS m/e: 550.3 (M+H$^+$).

Example 12

{(3S,4R)-3-(4-Chloro-phenyl)-4-[1-((S)-5-fluoro-pyridin-2-yloxy)-ethyl]-pyrrolidin-1-yl}-[1-(6-methyl-pyridazin-3-yl)-piperidin-4-yl]-methanone

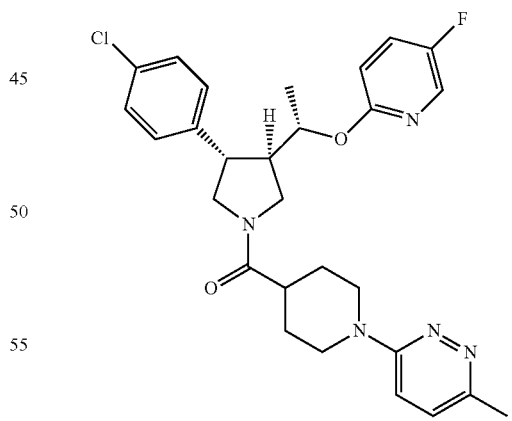

Amid coupling according to general procedure I:
Pyrrolidine intermediate: 2-{(S)-1-[(3R,4S)-4-(4-Chloro-phenyl)-pyrrolidin-3-yl]-ethoxy}-5-fluoro-pyridine (VII-B-2)
Carboxylic acid: 1-(6-Methyl-pyridazin-3-yl)-piperidine-4-carboxylic acid (commercially available),
ES-MS m/e: 524.3 (M+H$^+$).

Example 13

{(3S,4R)-3-(4-Chloro-phenyl)-4-[1-((S)-5-chloro-pyridin-2-yloxy)-ethyl]-pyrrolidin-1-yl}-(5'-methoxy-3,4,5,6-tetrahydro-2H-[1,2']bipyridinyl-4-yl)-methanone

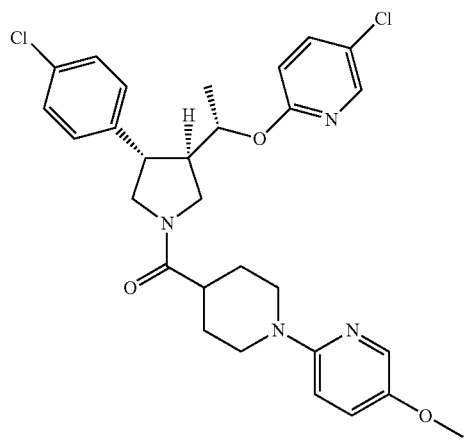 [SMILES: COc1ccc(N2CCC(C(=O)N3C[C@H]([C@H](C)Oc4ccc(Cl)cn4)[C@@H](c4ccc(Cl)cc4)C3)CC2)nc1]

Amid coupling according to general procedure I:
Pyrrolidine intermediate: 5-Chloro-2-{(S)-1-[(3R,4S)-4-(4-chloro-phenyl)-pyrrolidin-3-yl]-ethoxy}-pyridine (VII-B-1)
Carboxylic acid: 5'-Methoxy-3,4,5,6-tetrahydro-2H-[1,2]bipyridinyl-4-carboxylic acid (described herein above XIII-1),
ES-MS m/e: 555.2 (M+H$^+$).

Example 14

{(3S,4R)-3-(4-Chloro-phenyl)-4-[1-((S)-5-chloro-pyridin-2-yloxy)-ethyl]-pyrrolidin-1-yl}-[1-(6-methoxy-pyridazin-3-yl)-piperidin-4-yl]-methanone

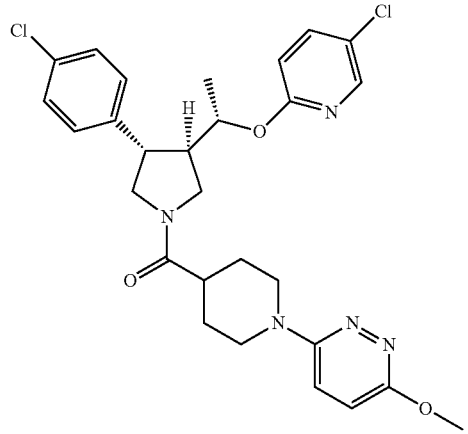 [SMILES: COc1ccc(N2CCC(C(=O)N3C[C@H]([C@H](C)Oc4ccc(Cl)cn4)[C@@H](c4ccc(Cl)cc4)C3)CC2)nn1]

Amid coupling according to general procedure I:
Pyrrolidine intermediate: 5-Chloro-2-{(S)-1-[(3R,4S)-4-(4-chloro-phenyl)-pyrrolidin-3-yl]-ethoxy}-pyridine (VII-B-1)
Carboxylic acid: 1-(6-Methoxy-pyridazin-3-yl)-piperidine-4-carboxylic acid (described herein above XIII-2),
ES-MS m/e: 556.1 (M+H$^+$).

Example 15

{(3S,4R)-3-(4-Chloro-phenyl)-4-[1-((S)-5-chloro-pyridin-2-yloxy)-ethyl]-pyrrolidin-1-yl}-(6'-methoxy-3,4,5,6-tetrahydro-2H-[1,3,']bipyridinyl-4-yl)-methanone

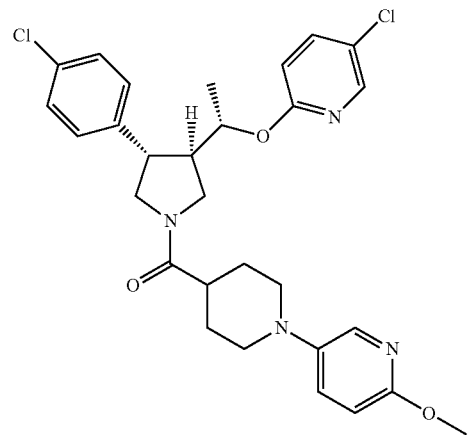 [SMILES: COc1ccc(N2CCC(C(=O)N3C[C@H]([C@H](C)Oc4ccc(Cl)cn4)[C@@H](c4ccc(Cl)cc4)C3)CC2)cn1]

Amid coupling according to general procedure I:
Pyrrolidine intermediate: 5-Chloro-2-{(S)-1-[(3R,4S)-4-(4-chloro-phenyl)-pyrrolidin-3-yl]-ethoxy}-pyridine (VII-B-1)
Carboxylic acid: 6'-Methoxy-3,4,5,6-tetrahydro-2H-[1,3']bipyridinyl-4-carboxylic acid (described herein above XIII-3),
ES-MS m/e: 555.2 (M+H$^+$).

Example 16

6-(4-{(3S,4R)-3-(4-Chloro-phenyl)-4-[1-((S)-5-fluoro-pyridin-2-yloxy)-ethyl]-pyrrolidine-1-carbonyl}-piperidin-1-yl)-pyridazine-3-carbonitrile

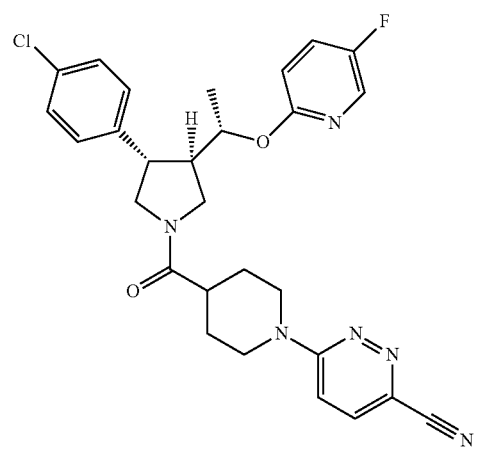

Coupling according to general procedure II:
Amine intermediate: {(3S,4R)-3-(4-Chloro-phenyl)-4-[1-((S)-5-fluoro-pyridin-2-yloxy)-ethyl]-pyrrolidin-1-yl}-piperidin-4-yl-methanone (VIII-B-2)
Heteroaryl: 6-Chloro-pyridazine-3-carbonitrile (commercially available),
ES-MS m/e: 535.2 (M+H$^+$).

Example 17

4-{(3S,4R)-3-(4-Chloro-phenyl)-4-[1-((S)-5-chloro-pyridin-2-yloxy)-ethyl]-pyrrolidine-1-carbonyl}-3,4,5,6-tetrahydro-2H-[1,2']bipyridinyl-6'-carbonitrile

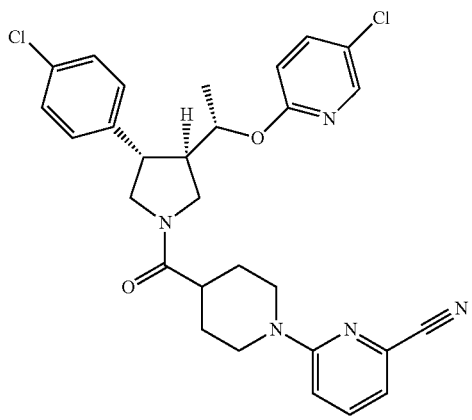 [SMILES: C[C@H](Oc1ccc(Cl)cn1)[C@H]1CN(C(=O)C2CCN(c3cccc(C#N)n3)CC2)C[C@@H]1c1ccc(Cl)cc1]

Coupling according to general procedure II:
Amine intermediate: {(3S,4R)-3-(4-Chloro-phenyl)-4-[1-((S)-5-chloro-pyridin-2-yloxy)-ethyl]-pyrrolidin-1-yl}-piperidin-4-yl-methanone (VIII-B-1)
Heteroaryl: 6-Chloro-pyridine-2-carbonitrile (commercially available),
ES-MS m/e: 550.4 (M+1-1').

Example 18

{(3S,4R)-3-(4-Chloro-phenyl)-4-[1-((S)-5-chloro-pyridin-2-yloxy)-ethyl]-pyrrolidin-1-yl}-[1-(5-methyl-[1,3,4]oxadiazol-2-yl)-piperidin-4-yl]-methanone

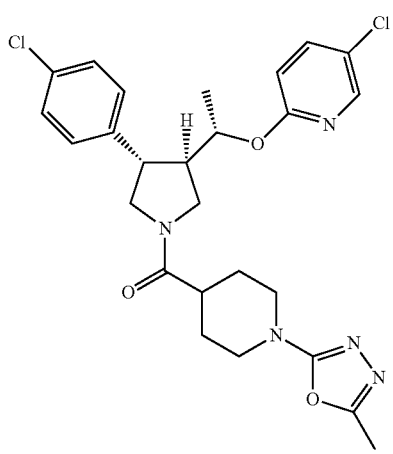 [SMILES: Cc1nnc(N2CCC(C(=O)N3C[C@H]([C@H](C)Oc4ccc(Cl)cn4)[C@@H](c4ccc(Cl)cc4)C3)CC2)o1]

Amid coupling according to general procedure I:
Pyrrolidine intermediate: 5-Chloro-2-{(S)-1-[(3R,4S)-4-(4-chloro-phenyl)-pyrrolidin-3-yl]-ethoxy}-pyridine (VII-B-1)
Carboxylic acid: 1-(5-Methyl-[1,3,4]oxadiazol-2-yl)-piperidine-4-carboxylic acid (described herein above XIII-4),
ES-MS m/e: 530.1 (M+H⁺).

Example 19

4-[(3R,4S)-3-[1-((S)-5-Cyano-pyridin-2-yloxy)-ethyl]-4-(3,4-difluoro-phenyl)-pyrrolidine-1-carbonyl]-3,4,5,6-tetrahydro-2H-[1,2']bipyridinyl-5'-carbonitrile

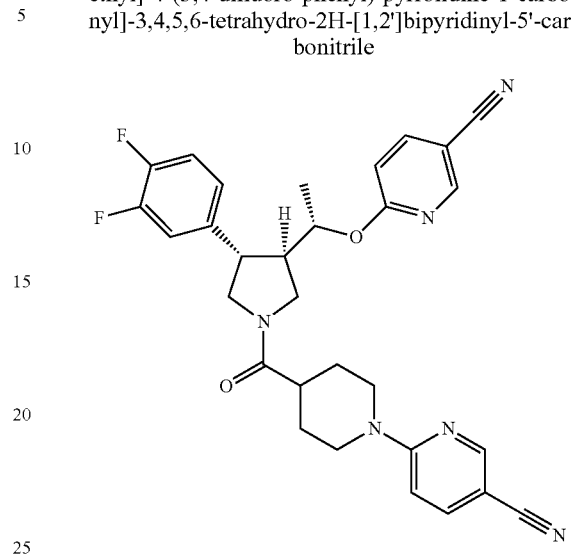

Amid coupling according to general procedure I:
Pyrrolidine intermediate: 6-{(S)-1-[(3R,4S)-4-(3,4-Difluoro-phenyl)-pyrrolidin-3-yl]-ethoxy}-nicotinonitrile (VII-B-4)
Carboxylic acid: 5'-Cyano-3,4,5,6-tetrahydro-2H-[1,2']bipyridinyl-4-carboxylic acid (commercially available),
ES-MS m/e: 542.4 (M+H⁺).

Example 20

4-[(3R,4S)-3-[1-((S)-5-Chloro-pyridin-2-yloxy)-ethyl]-4-(3,4-difluoro-phenyl)-pyrrolidine-1-carbonyl]-3,4,5,6-tetrahydro-2H-[1,2']bipyridinyl-5'-carbonitrile

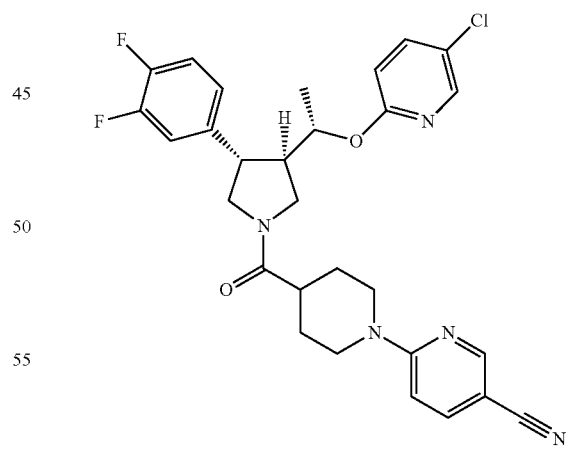

Amid coupling according to general procedure I:
Pyrrolidine intermediate: 5-Chloro-2-{(S)-1-[(3R,4S)-4-(3,4-difluoro-phenyl)-pyrrolidin-3-yl]-ethoxy}-pyridine (VII-B-3)
Carboxylic acid: 5'-Cyano-3,4,5,6-tetrahydro-2H-[1,2']bipyridinyl-4-carboxylic acid (commercially available),
ES-MS m/e: 552.0 (M+H⁺).

6-((S)-1-{(3R,4S)-4-(3,4-Difluoro-phenyl)-1-[1-(6-methyl-pyridazin-3-yl)-piperidine-4-carbonyl]-pyrrolidin-3-yl}-ethoxy)-nicotinonitrile

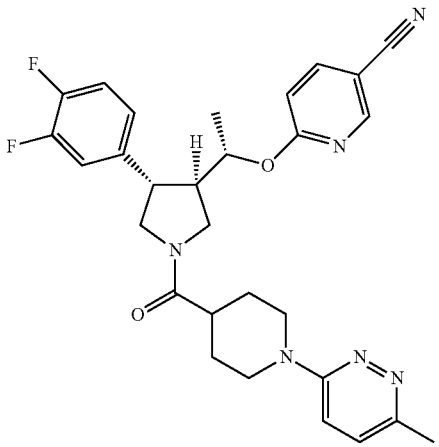 [SMILES: Cc1ccc(N2CCC(C(=O)N3C[C@H]([C@H](C)Oc4ccc(C#N)cn4)[C@@H](c4ccc(F)c(F)c4)C3)CC2)nn1]

Amid coupling according to general procedure I:
Pyrrolidine intermediate: 6-{(S)-1-[(3R,4S)-4-(3,4-Difluoro-phenyl)-pyrrolidin-3-yl]-ethoxy}-nicotinonitrile (VII-B-4)
Carboxylic acid: 1-(6-Methyl-pyridazin-3-yl)-piperidine-4-carboxylic acid (commercially available),
ES-MS m/e: 532.4 (M+1-1').

The invention claimed is:
1. A compound of formula I

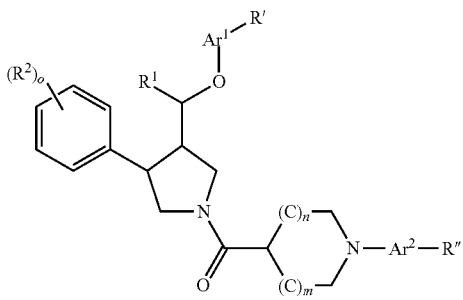

wherein
R$^1$ is hydrogen or lower alkyl;
R$^2$ is hydrogen, lower alkyl, lower alkyl substituted by halogen or is halogen or CN, and where o is 2 each R$^2$ is the same or different;
Ar$^1$ is aryl or heteroaryl;
Ar$^2$ is aryl or heteroaryl;
R' and R" are each independently hydrogen, lower alkyl, lower alkoxy, halogen, C(O)-lower alkyl, cyano or lower alkyl substituted by halogen;
m is 0, 1, or 2 when n is 0; or
m is 0 or 1 when n is 1;
n is 0 or 1; and
o is 1 or 2;
or a pharmaceutically active salt, racemic mixture, enantiomer, optical isomer or tautomeric form thereof.
2. The compound of claim 1, wherein n and m are 1.

3. The compound of claim 2, wherein Ar$^1$ and Ar$^2$ are both pyridinyl groups.
4. The compound of claim 3, selected from the group consisting of
4-{(3S,4R)-3-(4-chloro-phenyl)-4-[1-((S)-5-chloro-pyridin-2-yloxy)-ethyl]-pyrrolidine-1-carbonyl}-3,4,5,6-tetrahydro-2H-[1,2']bipyridinyl-5'-carbonitrile;
{(3S,4R)-3-(4-chloro-phenyl)-4-[1-((S)-5-chloro-pyridin-2-yloxy)-ethyl]-pyrrolidin-1-yl}-(5'-trifluoromethyl-3,4,5,6-tetrahydro-2H-[1,2']bipyridinyl-4-yl)-methanone;
1-(4-{(3S,4R)-3-(4-chloro-phenyl)-4-[1-((S)-5-chloro-pyridin-2-yloxy)-ethyl]-pyrrolidine-1-carbonyl}-3,4,5,6-tetrahydro-2H-[1,2']bipyridinyl-5'-yl)-ethanone;
4-{(3S,4R)-3-(4-chloro-phenyl)-4-[1-((S)-5-chloro-pyridin-2-yloxy)-ethyl]-pyrrolidine-1-carbonyl}-3,4,5,6-tetrahydro-2H-[1,2']bipyridinyl-4'-carbonitrile;
{(3S,4R)-3-(4-chloro-phenyl)-4-[1-((S)-5-chloro-pyridin-2-yloxy)-ethyl]-pyrrolidin-1-yl}-(5'-methoxy-3,4,5,6-tetrahydro-2H-[1,2']bipyridinyl-4-yl)-methanone;
{(3S,4R)-3-(4-chloro-phenyl)-4-[1-((S)-5-chloro-pyridin-2-yloxy)-ethyl]-pyrrolidin-1-yl}-(6'-methoxy-3,4,5,6-tetrahydro-2H-[1,3']bipyridinyl-4-yl)-methanone; and
4-[(3R,4S)-3-[1-((S)-5-chloro-pyridin-2-yloxy)-ethyl]-4-(3,4-difluoro-phenyl)-pyrrolidine-1-carbonyl]-3,4,5,6-tetrahydro-2H-[1,2']bipyridinyl-5'-carbonitrile.
5. The compound of claim 2, wherein Ar$^1$ is a pyridinyl group and R$^2$ is phenyl.
6. The compound of claim 5, which compound is
1-[4-(4-{(3S,4R)-3-(4-chloro-phenyl)-4-[1-((S)-5-chloro-pyridin-2-yloxy)-ethyl]-pyrrolidine-1-carbonyl}-piperidin-1-yl)-phenyl]-ethanone.
7. The compound of claim 2, wherein Ar$^1$ is a pyridinyl group and R$^2$ is a pyridazine group.
8. The compound of claim 7, selected from the group consisting of
6-(4-{(3S,4R)-3-(4-chloro-phenyl)-4-[1-((S)-5-chloro-pyridin-2-yloxy)-ethyl]-pyrrolidine-1-carbonyl}-piperidin-1-yl)-pyridazine-3-carbonitrile and
6-(4-{(3S,4R)-3-(4-chloro-phenyl)-4-[1-((S)-5-fluoro-pyridin-2-yloxy)-ethyl]-pyrrolidine-1-carbonyl}-piperidin-1-yl)-pyridazine-3-carbonitrile.
9. A pharmaceutical composition comprising a compound of formula I

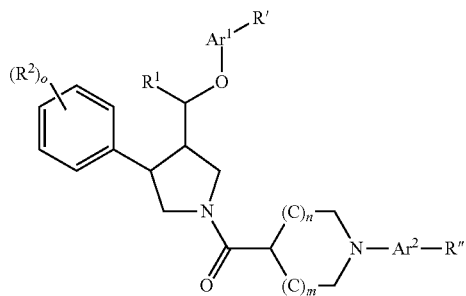

wherein
R$^1$ is hydrogen or lower alkyl;
R$^2$ is hydrogen, lower alkyl, lower alkyl substituted by halogen or is halogen or CN, and where o is 2 each R$^2$ is the same or different;
Ar$^1$ is aryl or heteroaryl;
Ar$^2$ is aryl or heteroaryl;

R' and R" are each independently hydrogen, lower alkyl, lower alkoxy, halogen, C(O)-lower alkyl, cyano or lower alkyl substituted by halogen;
m is 0, 1, or 2 when n is 0; or
m is 0 or 1 when n is 1;
n is 0 or 1; and
o is 1 or 2;
or a pharmaceutically active salt, racemic mixture, enantiomer, optical isomer or tautomeric form thereof and a pharmaceutically acceptable carrier.

* * * * *